US008735662B2

(12) United States Patent  (10) Patent No.: US 8,735,662 B2
van Schijndel  (45) Date of Patent: May 27, 2014

(54) LETTUCE VARIETY SALMON

(75) Inventor: Jan van Schijndel, CG's-Gravenzande (NL)

(73) Assignee: Nunhems B.V., AC Nunhem (NL)

( * ) Notice: Subject to any disclaimer, the term of this patent is extended or adjusted under 35 U.S.C. 154(b) by 293 days.

(21) Appl. No.: 13/108,375

(22) Filed: May 16, 2011

(65) Prior Publication Data

US 2012/0144513 A1  Jun. 7, 2012

(51) Int. Cl.
*A01H 1/00* (2006.01)
*A01H 4/00* (2006.01)
*A01H 5/00* (2006.01)
*A01H 5/10* (2006.01)
*C12N 5/04* (2006.01)

(52) U.S. Cl.
USPC ............ 800/305; 800/260; 800/298; 435/410

(58) Field of Classification Search
None
See application file for complete search history.

(56) References Cited

U.S. PATENT DOCUMENTS

| | | | |
|---|---|---|---|
| 5,349,124 | A | 9/1994 | Fischhoff |
| 5,378,619 | A | 1/1995 | Rogers |
| 5,500,365 | A | 3/1996 | Fischhoff |
| 5,563,055 | A | 10/1996 | Townsend |
| 5,633,435 | A | 5/1997 | Barry |
| 5,689,052 | A | 11/1997 | Brown |
| 5,880,275 | A | 3/1999 | Fischhoff |
| 5,977,443 | A | 11/1999 | Jansen |
| 8,404,936 | B2 * | 3/2013 | Skrsyniarz ............... 800/305 |
| 2008/0222949 | A1 | 9/2008 | Bissonnette |
| 2009/0106867 | A1 | 4/2009 | Moor |
| 2009/0271897 | A1 | 10/2009 | Gibson |

FOREIGN PATENT DOCUMENTS

| | | |
|---|---|---|
| EP | 1197137 | 4/2002 |
| WO | 9931248 | 6/1999 |

OTHER PUBLICATIONS

F.A. Van Eeuwijk et al., Statistical aspects of essential derivation, with illustrations based on lettuce and barley, Euphytica (2004) vol. 137, pp. 129-137.

H.J. Hill et al., Primed Lettuce Seeds Exhibit Increased Sensitivity to Moisture Content During Controlled Deterioration, HortScience (2007) 42(6), pp. 1436-1439.

Peter Halmer, Commercial seed treatment technology in "Seed technology and its biological basis", Michael Black Eds. (2000), pp. 257-286.

Louise Jackson et al., Iceberg Lettuce Production in California, Publication 7215, ISBN 978-1-60107-007-4, (1996).

Louise Jackson et al., Leaf Lettuce Production in California, Publication 7216 ISBN 978-1-60107-008-1, (1996).

Takeru Gonai et al., Abscisic acid in the thermoinhibition of lettuce seed germination and enhancement of its catabolism by gibberellin, Journal of Experimental Botany (2004) vol. 55, No. 394, pp. 111-118.

Arlette Reynaerts et al., Engineered genes for fertility control and their application in hybrid seed production, Scientia Horticulturae (1993) 55 (1-2), pp. 125-139.

Marie-Christine Chupeau et al., Transgenic Plants of Lettuce (*Lactuca sativa*) obtained through Electroporation of Protoplasts, Bio/Technology 7 (1989), pp. 503-508.

Ritsuko Murakami et al., Histological Observations on the Formulation of Meristematic Colonies Derived from Lettuce (*Lactuca sativa* L) Protoplasts, Plant Tissue Culture Letters (1996) 13(3), pp. 339-341.

James A. Elliot et al., Collapse of Single-Wall Carbon Nanotubes is Diameter Dependent, Physical Review Letters (2004) vol. 92, pp. 095501-095504.

Pil S. Choi et al., Genetic transformation and plant regeneration of watermelon using *Agrobacterium tumefaciens*, Plant Cell Rep (1994) 13, pp. 344-348.

Ian S. Curtis et al., Genomic male sterility in lettuce, a baseline for the production of F, hybrids, Plant Science Limerick (1996) 113(1), pp. 113-119.

Peter Vos et al., AFLP: a new technique for DNA fingerprinting 1995, Nucleic Acids Research (1995) vol. 23, No. 21, pp. 4407-4414.

Rudy A. Dekeyser et al., Transient Gene Expression in Intact and Organized Rice Tissues, The Plant Cell (1990) vol. 2, pp. 591-602.

William R. Marcotte et al., Abscisic Acid-Responsive Sequences from the Em Gene of Wheat, The Plant Cell (1989) vol. 1, pp. 969-976.

Cris Kuhlemeier et al.,The Pea rbcS-3A Promoter Mediates Light Responsiveness but not Organ Specificity Cris, The Plant Cell (1989) vol. 1, pp. 471-478.

Serik Omirulleh et al., Activity of a chimeric promoter with the doubled CaMV 35S enhancer element in protoplast-derived cells and transgenic plants in maize, Plant Molecular Biology (1993) vol. 21, pp. 415-428.

Ingo Potrykus et al, Direct gene transfer to cells of a graminaceous monocot, Mol Gen Genet (1985) vol. 199, pp. 183-188.

S. Rosahl et al., Expression of a tuber-specific storage protein in transgenic tobacco plants: demonstration of an esterase activity, The Embo Journal (1987) vol. 5 No. 5, pp. 1155-1159.

Anton R. Schäffner et al., Maize rbcS Promoter Activity Depends on Sequence Elements Not Found in Dicot rbcS Promoters, The Plant Cell (1991) vol. 3, pp. 997-1012.

(Continued)

*Primary Examiner* — Eileen B O Hara

(57) ABSTRACT

The present invention relates to a lettuce variety NUN 7824 LT (referred to as "Salmon") having resistance against downy mildew (*Bremia lactucae*) and lettuce aphid (*Nasonovia ribisnigri*) and which has very intense red colored and glossy leaves. The invention further relates to methods for producing the new lettuce variety and representative seed having been deposited under Accession No. NCIMB_____.

23 Claims, 3 Drawing Sheets

(56) References Cited

OTHER PUBLICATIONS

Figure 2:
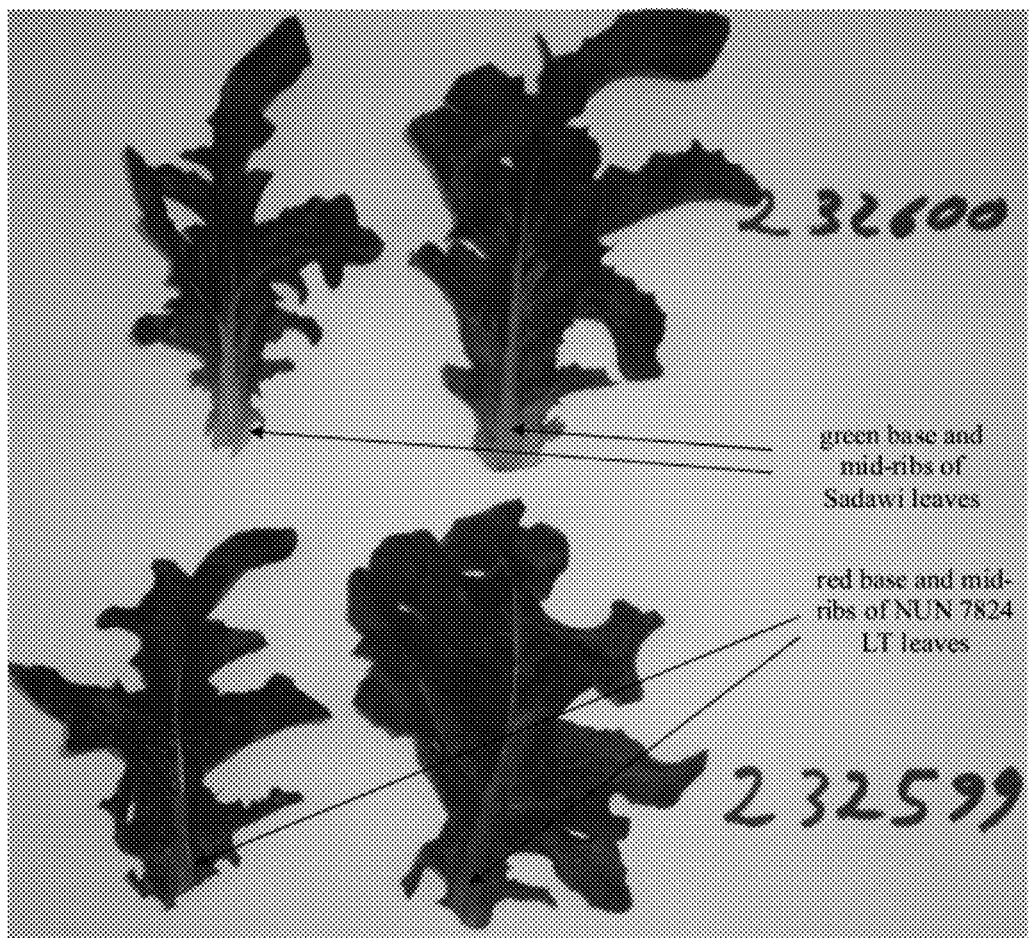

J. P. Schernthaner et al., Endosperm-specific activity of a zein gene promoter in transgenic tobacco plants, The Embo Journal (1988) vol. 7 No. 5, pp. 1249-1255.
Barbara Siebertz et al., cis-Analysis of the Wound-Inducible Promoter wun7 in Transgenic Tobacco Plants and Histochemical Localization of Its Expression, The Plant Cell (1989) vol. 1, pp. 961-968.
June Simpson, Light-inducible and tissue-specific expression of a chimaeric gene under control of the 5'-flanking sequence of a pea chlorophyll a/bbinding protein gene, The Embo Journal (1985) vol. 4, pp. 2723-2729.
Rie Terada et al., Expression of CaMV35S-GUS gene in transgenic rice plants, Mol Gen Genet (1990) vol. 220, pp. 389-392.
Hirofumi Uchimiya, Expression of a foreign gene in callus derived from DNA-treated protoplasts of rice (*Oryza sativa* L), Mol Gen Gene (1986) vol. 204, pp. 204-207.
Judy Callis et al, Heat Inducible Expression of a Chimeric Maize hsp7OCAT Gene in Maize Protoplasts1, Plant Physiol. (1988) vol. 88, pp. 965/968.
Mauricio M. Bustos et al., Regulation of ,β-Glucuronidase Expression in Transgenic Tobacco Plants by an A/T-Rich, cis-Acting Sequence Found Upstream of a French Bean , β-Phaseolin Gene, The Plant Cell (1989) vol. 1, pp. 839-853.
Gynheung An et al., Organ-Specific and Developmental Regulation of the Nopaline Synthase Promoter in Transgenic Tobacco Plants, Plant Physiol (1988) vol. 88, pp. 547-552.
F.J.M. Bonnier et al., New sources of major gene resistance in Lactuca to *Bremia lactucae*, Euphytica (1992) vol. 61, pp. 203-211.
Hillel Fromm et al., An Octopine Synthase Enhancer Element Directs Tissue-Specific Expression and Binds ASF-1, a Factor from Tobacco Nuclear Extracts, The Plant Cell (1989) vol. 1, pp. 977-984.
Graca Miguel et al., Anthocyanin Concentration of "Assaria" Pomegranate Fruits During Different Cold Storage Conditions, Journal of Biomedicine and Biotechnology (2004) vol. 5, pp. 338-342.
Harry Klee et al., Vectors for Transformation of Higher Plants, Bio/Technology (1985) vol. 3, pp. 637-642.
Robert T. Fraley et al., The Sev System: A new Disarmed ti Plasmid Vector System for Plant Transformation, Bio/Technology (1985) vol. 3, pp. 629-635.
Wiliam R. Marcotte et al., Regulation of a wheat promoter by abscisic acid in rice protoplasts, Nature (1988) vol. 335, pp. 454-457.
Joan T. Odell et al., Identification of DNA sequences required for activity of the cauliflower mosaic virus 35S promoter, Nature (1985) vol. 313, pp. 810-812.
Michael E. Fromm et al., Stable transformation of maize after gene transfer by electroporation, Nature (1986) vol. 319, pp. 791-793.
P. Ellul et al., The expression of the *Saccharomyces cerevisiae* HAL1 gene increases salt tolerance in transgenic watermelon [*Citrullus lanatus* (Thunb.) Matsun. & Nakai.], Theor. Appl. Genet (2003) vol. 107, pp. 462-469.
J. Molinier et al., Transient expression of ipt gene enhances regeneration and transformation rates of sunflower shoot apices (*Helianthus annuus* L.), Plant Cell Rep. (2002) vol. 21, pp. 251-256.
K. Van Ettekoven et al., Identification and denomination of "new" races of *Bremia lactuce*, Eucarpia Leafy Vegetables (1999), pp. 171-175.
USDA descriptors (www.ams.usda.gov/AMSv1.0/getfile?dDocName=stelprdc5069208), (2009).
UPOV descriptors, "Guidelines for the Conduct of Tests for Distinctness, Uniformity and Stability," TG/013/10 (http://www.upov.int/edocs/tgdocs/en/tg013.pdf), (2011).

\* cited by examiner

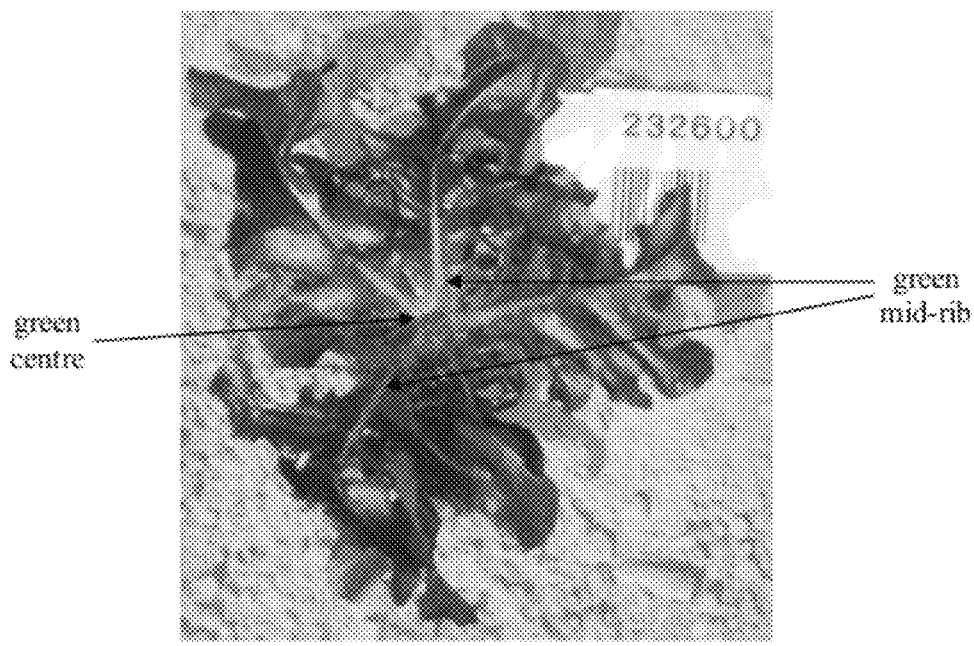
Figure 1a: Sadawi plant
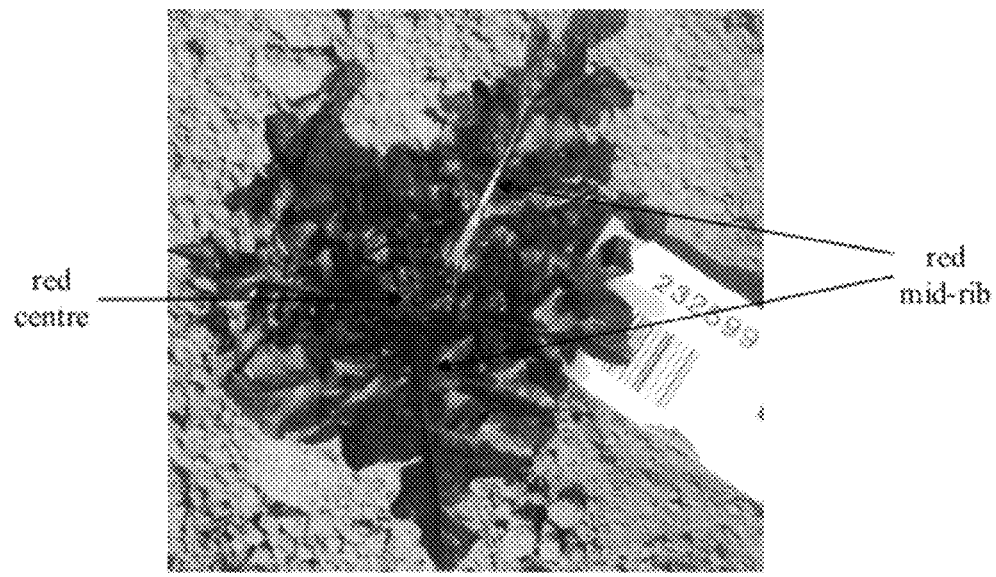
Figure 1b: NUN 7824 LT

Differences in red color of Sadawi (232600) and NUN 7824 LT (232599, only visible as 2325)

LETTUCE VARIETY SALMON

FIELD OF THE INVENTION

The present invention relates to the field of plant breeding. In particular, the invention provides for a new and distinct variety of lettuce designated NUN 7824 LT (or "Salmon") which exhibits resistance against downy mildew (*Bremia lactucae*) and lettuce aphid (*Nasonovia ribisnigri*). The variety is distinct from the most similar variety Sadawi (sold by Enza as baby leaf lettuce variety) in its white (silver grey) seed color (Sadawi: black seed color (grey brown)) and, e.g., its higher anthocyanin concentration in fourth leaves and mature leaves, the higher glossiness of mature leaves and the more intensive red color of said mature leaves.

Lettuce varieties are susceptible to a number of diseases such as downy mildew, *Sclerotinia* rot, Botrytis, powdery mildew, anthracnose, bottom rot, corky root rot, Bacterial soft rot (*Pseudomonas* spp. and others), Bacterial Leaf Spot, *Verticillium* wilt, lettuce mosaic virus, big vein, beet western yellows and aster yellows, lettuce aphid (*Nasonovia ribisnigri*), Cabbage loopers, Green Peach aphid, Pea Leafminer and Root aphids. These diseases result in millions of dollars of lost lettuce crop throughout the world every year.

Of the various diseases that affect lettuce varieties, downy mildew (*Bremia lactucae*) is the most highly destructive of lettuce grown at relatively low temperature and high humidity. Downy mildew is caused by a fungus, Bremia lactucae Regal, which can be one of the following strains: NL1, NL2, NL4, NL5, NL6, NL7, NL10, NL12, NL13, NL14, NL15, NL16, Bl:17, Bl:21 and Bl:23 (Van Ettekoven, K. et al., "Identification and denomination of 'new' races of Bremia lactucae." In: Lebeda, A. and Kristkova, E (eds.), Eucarpia Leafy Vegetables, 1999, Palacky University, Olomouc, Czech Republic, pp. 171-175).

Downy mildew causes pale, angular, yellow areas bounded by veins on the upper leaf surfaces. Sporulation occurs on the opposite surface of the leaves. The lesions eventually turn brown, and they may enlarge and coalesce. These symptoms typically occur first on the lower leaves of the lettuce, but under ideal conditions may move into the upper leaves of the head. When the fungus progresses to this degree, the head cannot be harvested. Less severe damage requires the removal of more leaves than usual, especially when the lettuce reaches its final destination.

Lifestyles change and the demand from restaurants and catering firms for colorful and interesting garnish for ready-to-use processed salads continue to rise. As a result, there is a demand for breeding companies to develop new varieties with prominent color and a wide variety of texture.

FIGURES

FIG. 1: Exemplary vertical view on lettuce variety Sadawi (Figure 1a) and variety NUN 7824LT (FIG. 1b).

FIG. 2: Exemplary comparison of Sadawi and NUN 7824 leaves.

Figure 3:
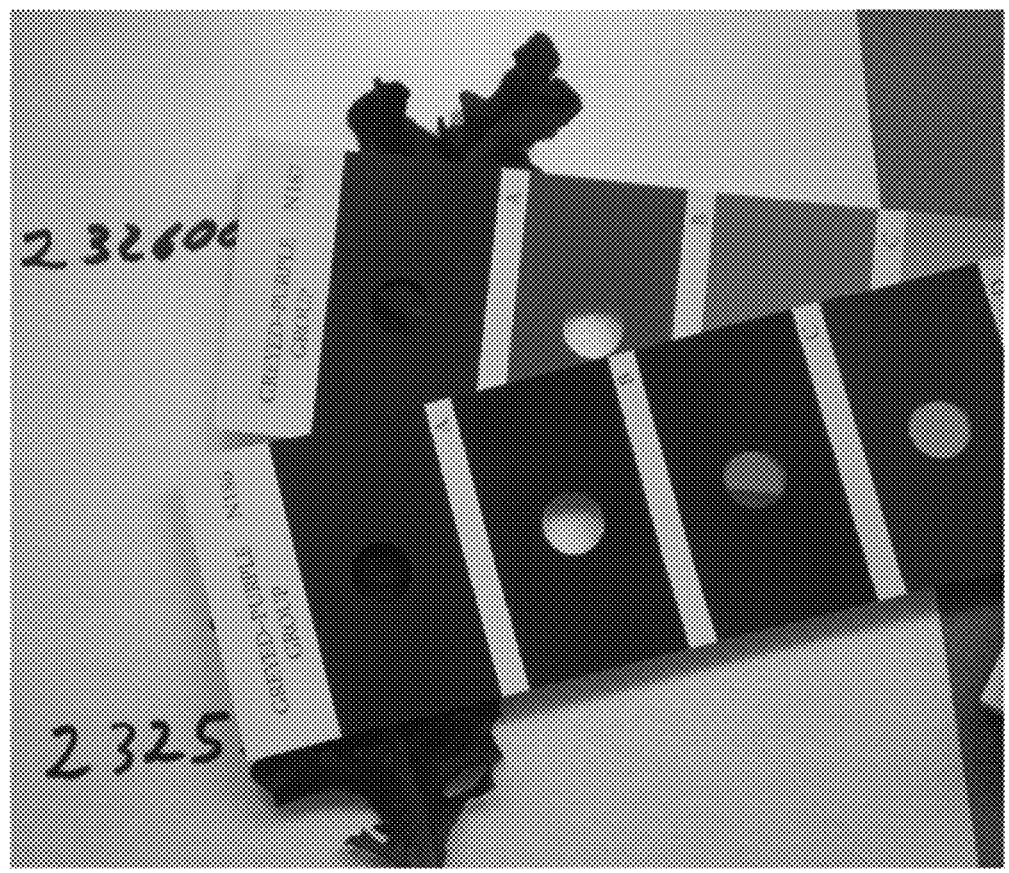

FIG. 3: Exemplary comparison of leave color of Sadawi and NUN 7824 LT using RHS colour chart: 2007.

SUMMARY OF THE INVENTION

The invention provides for a new variety of loose-leaf lettuce designated NUN 7824 LT, representative seed of said variety having been deposited under Accession Number NCIMB 42217. The variety exhibits resistance against downy mildew (*Bremia lactucae*) as well as lettuce aphid (*Nasonovia ribisnigri*) and has very intensive red mature leaves.

The invention also provides for seeds of the new variety, representative seed of said variety having been deposited under Accession Number NCIMB 42217, plants produced from growing the seeds and plant parts obtainable from the grown plants, such as (harvested) leaves, or parts of the leaves. Non-limiting examples for parts of said plant are microspores, pollen, ovaries, flowers, stalks, ovules, leaves, shoots, seeds, embryos, embryo sacs cuttings, roots, cuttings, stems, cells, protoplasts, meristems, buds or parts of any of these such as parts of leaves. In some embodiments, parts of a lettuce plant designated NUN 7824 LT are provided which are suitable for sexual reproduction or vegetative reproduction, or a tissue or cell culture of a lettuce plant designated NUN 7824 LT is provided.

In further aspects, the invention provides a lettuce plant which is grown from a seed of the invention, a plant regenerated from a part of the lettuce plant designated NUN 7824 LT which is suitable for vegetative reproduction or regenerated from a cell or tissue culture of a plant designated NUN 7824 LT, whereby said lettuce plant is resistant against downy mildew (*Bremia lactucae* Regal) BL:1 to BL:27, resistant against lettuce aphid (*Nasonovia ribisnigri*) Nr0 and has very intensive red colored mature leaves.

In further aspects, the invention provides methods of producing a lettuce plant, comprising crossing or selfing the lettuce plant designated NUN 7824 LT with a second lettuce plant one or more times, and selecting progeny from said crossing or selfing.

Also provided is a progeny of lettuce plant designated NUN 7824 LT obtained by further breeding with said variety designated NUN 7824 LT. Said progeny has at least the essential physiological and morphological characteristics selected from the group consisting of resistance against downy mildew (*Bremia lactucae*) Bl:1 to Bl:27 and lettuce aphid (*Nasonovia ribisnigri*) Nr:0 and very intensive red colored fourth and mature leaves. In one embodiment, said progeny further has at least one of the physiological and morphological characteristics selected from the group consisting of white to silver grey seed color, broad shape of cotyledons (according to USDA descriptors), higher concentration of anthocyanin in fourth leaves and mature leaves compared to fourth leaves and mature leaves of lettuce variety Sadawi, glossy mature leaves (according to USDA descriptors), higher average head weight of at least 5% at mature harvest stage compared to the average head weight of lettuce variety Sadawi at the same mature harvest stage, when grown under the same conditions.

Moreover, also an Essentially Derived Variety (EDV) of a lettuce plant designated NUN 7824 LT is provided having one, two, three or more than three physiological and/or morphological characteristics which are different from those of NUN 7824 LT but which otherwise has all the essential physiological and morphological characteristics of a lettuce plant designated NUN 7824 LT selected from the group consisting of resistance against downy mildew (*Bremia lactucae*) BI:1 to BI:27, resistance against lettuce aphid (*Nasonovia ribisnigri*) Nr:0 and very intensive red colored mature leaves.

In another aspect the invention provides a method of producing a hybrid lettuce seed comprising crossing a first parent lettuce plant with a second parent lettuce plant and harvesting the resultant hybrid lettuce seed, wherein said first parent lettuce plant or said second parent lettuce plant is a lettuce plant designated NUN 7824 LT.

Also provided is hybrid lettuce plant produced from crossing a first parent lettuce plant with a second parent lettuce plant and harvesting the resultant hybrid lettuce seed, wherein said first parent lettuce plant or said second parent lettuce plant is a plant designated NUN 7824 LT.

In another aspect the invention refers to packages, e.g., a container, a bag and the like, comprising at least one of the following: seeds or seed pellets of lettuce variety designated NUN 7824 LT, lettuce plant(s) designated NUN 7824 LT, parts thereof, progeny of a lettuce plant designated NUN 7824 LT, parts thereof, EDVs a plant designated NUN 7824 LT or parts thereof.

Also provided is a food or feed product comprising at least a part of a lettuce plant designated NUN 7824 LT.

In another aspect the invention provides a method of introducing a single locus conversion into a plant designated NUN 7824 LT, representative seed of which having been deposited under Accession Number NCIMB 42217, comprising (a) crossing a plant designated NUN 7824 LT with a second plant comprising a desired single locus to produce F1 progeny plants;

(b) selecting F1 progeny plants that have the single locus to produce selected F1 progeny plants;

(c) crossing the selected progeny plants with at least a first plant of NUN 7824 LT, representative seed of which having been deposited under Accession Number NCIMB 42217, to produce backcross progeny plants;

(d) selecting backcross progeny plants that have the single locus and essential physiological and morphological characteristics selected from the group consisting of resistance against downy mildew (*Bremia lactucae*) BI:1 to BI:27, resistance against lettuce aphid (*Nasonovia ribisnigri*) Nr:0 and very intensive red colored mature leaves of a plant designated NUN 7824 LT to produce selected backcross progeny plants; and (e) repeating steps (c) and (d) one or more times in succession to produce selected second or higher backcross progeny plants that comprise the single locus and otherwise comprise at least the essential physiological and morphological characteristics selected from the group consisting of resistance against downy mildew (*Bremia lactucae*) BI:1 to BI:27, resistance against lettuce aphid (*Nasonovia ribisnigri*) Nr:0 and very intensive red colored mature leaves of a plant designated NUN 7824 LT.

In one embodiment, said single locus confers a trait, wherein the trait is pest resistance or disease resistance such as resistance against *Nasonovia ribisnigri* NR:1. Further pest or disease resistances are, e.g., resistance against downy mildew, *Sclerotinia* rot, botrytis, powdery mildew, anthracnose, bottom rot, corky root rot, lettuce mosaic virus, big vein, lettuce aphid, beet western yellows and aster yellows, *Sclerotinia* minor (leaf drop), *Sclerotinia sclerotiorum* (leaf drop), *Rhizoctonia solani* (bottom drop), *Erysiphe cichoracearum* (powdery mildew), *Fusarium oxysporum* f. sp. *Lactucae* (fusarium wilt), lettuce infectious yellows virus (LIYV), lettuce mosaic virus (LMV), Cucumber mosaic virus (CMV), Beet western yellows virus (BWYV), and Alfalfa mosaic virus (AMV).

DETAILED DESCRIPTION

"Lettuce" refers herein to plants of the species *Lactuca sativa* L.

The terms "lettuce plant designated NUN 7824 LT" or "variety designated NUN 7824 LT" refer to a lettuce plant/variety of lettuce, representative seed of which having been deposited under Accession Number NCIMB 42217.

"USDA descriptors" are the plant variety descriptors described for lettuce in the "Objective description of Variety Lettuce (*Lactuca sativa* L.)", ST-470-1 (dated Jul. 1, 2009) as published by U.S. Department of Agriculture, Agricultural Marketing Service, Science and Technology, Plant Variety Protection Office, Beltsville, Md. 20705 (available on the world wide web at www.ams.usda.gov/AMSv1.0/) and which can be downloaded from the world wide web at www.ams.usda.gov/AMSv1.0/getfile?dDocName=stelprdc5069208, and is herein incorporated by reference in its entirety.

"UPOV descriptors" are the plant variety descriptors described for lettuce in the "Guidelines for the Conduct of Tests for Distinctness, Uniformity and Stability," TG/013/10 (Geneva 2006), as published by UPOV (International Union for the Protection of New Varieties and Plants, available on the world wide web at upov.int) upov.int/en/publications/tg_rom/tg_index.html, and is herein incorporated by reference in its entirety Likewise, "UPOV methods" to determine specific parameters for the characterization of lettuce are described at upov.int.

As used herein, the term "plant" includes the whole plant or any parts such as plant organs (e.g., harvested or non-harvested leaves, etc.), plant cells, plant protoplasts, plant cell or tissue cultures from which whole plants can be regenerated, plant callus, plant cell clumps, plant transplants, seedlings, plant cells that are intact in plants, plant clones or micro-propagations, or parts of plants (e.g., harvested tissues or organs), such as plant cuttings, vegetative propagations, embryos, pollen, ovules, flowers, leaves, heads, seeds, clonally propagated plants, roots, stems, stalks, root tips, grafts, parts of any of these and the like, or derivatives thereof, preferably having the same genetic make-up (or very similar genetic make-up) as the plant from which it is obtained. Also any developmental stage is included, such as seedlings, cuttings prior or after rooting, mature and/or immature plants or mature and/or immature leaves.

"Harvested plant material" refers herein to plant parts (e.g., leaves detached from the whole plant) which have been collected for further storage and/or further use.

"Head" as used herein refers to lettuce heads, i.e., the plant without the root system, for example substantially all harvested leaves (although this variety is a "loose-leaf" type). Encompassed are immature leaves (e.g. "baby leaf") and mature leaves.

"Harvested seeds" refers to seeds harvested from a line or variety, e.g., produced after self-fertilization or cross-fertilization and collected.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Progeny" as used herein refers to plants derived from a plant designated NUN 7824 LT. Progeny may be derived by regeneration of cell or tissue culture or parts of a plant designated NUN 7824 LT or selfing of a plant designated NUN 7824 LT or by growing seeds of a plant designated NUN 7824 LT. In further embodiments, progeny may also encompass plants derived from crossing of at least one plant designated NUN 7824 LT with another lettuce plant of the same variety or another lettuce or wild lettuce variety, backcrossing, inserting of a locus into a plant or mutation.

An "Essentially Derived Variety" (EDV) shall be deemed to be essentially derived from another variety, "the initial variety", under the following circumstances: (i) it is predominantly derived from the initial variety, or from a variety that is itself predominantly derived from the initial variety, while retaining the expression of the essential characteristics that result from the genotype or combination of genotypes of the initial variety, i.e., at least resistance against downy mildew (*Bremia lactucae*) Bl:1 to Bl:27 and lettuce aphid (*Nasonovia ribisnigri*) Nr:0 and very intensive red colored leaves; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcrossing, or transformation by genetic engineering.

"Plant line" is for example a breeding line which can be used to develop one or more varieties.

"Hybrid" refers to the seeds harvested from crossing one plant line or variety with another plant line or variety.

"$F_1$ Hybrid" refers to the first generation progeny of the cross of two nonisogenic plants.

"Crossing" refers to the mating of two parent plants.

"Backcrossing" refers to a process in which a breeder repeatedly crosses hybrid progeny, for example a first generation hybrid ($F_1$), back to one of the parents of the hybrid progeny. Backcrossing can be used to introduce one or more single locus conversions from one genetic background into another.

"Cross-pollination" refers to fertilization by the union of two gametes from different plants.

"Regeneration" refers to the development of a plant from tissue culture.

"Selfing" refers to self-pollination of a plant, i.e., the transfer of pollen from the anther to the stigma of the same plant.

"Single Locus Converted (Conversion) Plant": Plants which are developed by a plant breeding technique called backcrossing, wherein essentially all of the desired morphological and physiological characteristics of a lettuce variety are recovered in addition to the characteristics of the single locus transferred into the variety via the backcrossing technique and/or by genetic transformation.

"Substantially Equivalent" refers to a characteristic that, when compared, does not show a statistically significant difference (e.g., p=0.05) from the mean.

"Tissue Culture" refers to a composition comprising isolated cells of the same or a different type or a collection of such cells organized into parts of a plant.

"Transgene" refers to a genetic locus comprising a sequence which has been introduced into the genome of a lettuce plant by transformation.

"Average" refers herein to the arithmetic mean.

As used herein, "resistance against *Bremia lactucae*" is defined as the capacity of a plant to resist infection by at least strains BL1 to BL 27 of the *Bremia lactucae* Regal in all stages between the seedling stage and the harvestable plant stage. Resistance against *Bremia lactucae* is typically tested by two interchangeable methods, described by Bonnier, F. J. M. et al. (Euphytica, 61(3):203-211, 1992 which is herewith incorporated by reference). One method involves inoculating 7-day old seedlings with spores of individual Bremia races (e.g. selected from Bl:1 to Bl:27), and observing sporulation 10 to 14 days later. The other method involves inoculating leaf discs with a diameter of 18 mm obtained from a non-senescent, fully grown true leaf and observing sporulation 10 days later.

As used herein, "resistance against *Nasonovia ribisnigri*" (Mosley), or lettuce aphid, is defined as the plant characteristic which results in a non-feeding response of the lettuce aphid Nr:0 on the leaves of the plant in all stages between 5 true-leaf stage and harvestable plant stage (U.S. Pat. No. 5,977,443 to Jansen, J. P. A., "Aphid Resistance in Composites," p. 12, 1999; incorporated herein by reference). Resistance is typically tested by spreading at least ten aphids on a plant in a plant stage between 5 true leaves and harvestable stage, and observing the density of the aphid population on the plant as well as the growth reduction after 14 days in a greenhouse, with temperature settings of 23° C. in daytime and 21° C. at night. Day length is kept at 18 hours by assimilation lights.

All cultivated forms of lettuce belong to the highly polymorphic species *Lactuca sativa* that is grown for its edible head and leaves. *Lactuca sativa* is in the Cichoreae tribe of the Asteraceae (Compositae) family. Lettuce is related to chicory, sunflower, aster, dandelion, artichoke and chrysanthemum. L. sativa is one of about 300 species in the genus *Lactuca*.

The present invention provides a new type of lettuce (*Lactuca sativa*) variety, designated NUN 7824 LT (referred to as "Salmon"). Lettuce variety designated NUN 7824 LT exhibits a combination of resistance against at least strains Bl:1 to Bl:27 of downy mildew (*Bremia lactucae*), as well as lettuce aphid *Nasonovia ribisnigri* NR:0 and has very intense red colored leaves.

The development of a red color in many plant species is dependent on the production of anthocyanin. The skilled person is well aware of methods to quantify the amount of anthocyanin form, e.g., Graça Miguel J Biomed Biotechnol. 2004(5): 338-342 which is herewith incorporated by reference.

The plants of NUN 7824 LT are most similar to the commercially available variety Sadawi, which is a red colored, loose-leaf lettuce variety sold by Enza Zaden. However, NUN 7824 LT differs from Sadawi in a number of morphological and/or physiological characteristics. Moreover, NUN 7824 LT is easily distinguishable from Sadawi in its seeds on the one hand and, when grown under the same environmental conditions, in, e.g., its leaf color and glossiness (see also Table 1).

Essential morphological and/or physiological characteristics of a lettuce plant designated NUN 7824 LT are its resistance against downy mildew (*Bremia lactucae* Regal) BL:1 to BL:27, resistance against lettuce aphid (*Nasonovia ribisnigri*) Nr:0 and its very intensive red colored leaves. Thus, the term "having at least the essential morphological and physiological characteristics" as used herein refers to at least these three characteristics mentioned above.

The term "very intensive red colored" when referring to the color of leaves of NUN 7824 LT means that leaves of NUN 7824 LT, such as fourth leaves and/or mature leaves, are overall more red than leaves of Sadawi-plants. For example, the basis of the Sadawi-leaves (the area of the leave which is attached to the centre of the plant) and their mid-ribs are essentially green whereas the leaves of NUN 7824 LT including their basis and mid-ribs are essentially red. Moreover, the overall color of leaves of NUN 7824 LT is more intensive, i.e. darker than the color of Sadawi leaves. The overall more red colored leaves of NUN 7828 LT yields in a plant having a more homogenous allocation of a very intensive red color of the plant. In contrast, a plant designated Sadawi exhibits a green core in the centre of said plant which has an area when looking vertically on the plant covers an area which exceeds at least 1.5 times, 2 times, 3 times, 4 times, 5 times the area located in the centre of a plant designated NUN 7824 LT which is possibly green. In one embodiment, the mid-ribs of all mature leaves of NUN 7824 LT are essentially red, e.g., less than 10%, 5%, 3% of a mid-rib is not red but green. In one embodiment, less than 10%, 5%, 3% of the first cm of a leave when cutting said leave at the center of the plant is not red at its basis (the part of the leave with which it is attached to the centre of the plant.

Without limiting the scope of the present invention and for demonstrating the present invention, FIG. 1 shows the centre of a randomly selected Sadawi plant in comparison to a randomly selected plant designated NUN 7824 LT. Both plants were grown under the same conditions. The centre of the Sadawi plant is clearly green and exhibit leaves having a greenish mid-rib whereas the plant designated NUN 7824 LT shows an overall very intensive red color and leaves having very red colored mid-ribs.

In addition, without limiting the scope of the present invention, FIG. 2 shows two exemplary leaves of Sadawi (232600) and two exemplary leaves of NUN 7824 LT (232599). As apparent, the bases of the Sadawi leaves are green whereas the bases of the leaves of NUN 7826 LT are red. The same is apparently visible for the mid-ribs.

FIG. 3, without limiting the present invention, shows an exemplary Sadawi leaf and a color chart N187 and a leaf of NUN 7826 LT and a color chart N186. N186 is clearly darker than N187. Moreover, the leaf of NUN 7826 LT is even darker than the color chart whereas the leaf of Sadawi has a slightly brighter color compared with the N187 color chart.

Without being bound, it is believed that the darker more intensive red color results from a higher anthocyanin concentration in leaves, e.g., fourth leaves and/or mature leaves of NUN 7824 LT, compared to leaves of Sadawi, e.g., fourth leaves and/or mature leaves.

The term "having at least the essential morphological and physiological characteristics" as used herein refers to at least these three characteristics mentioned above. Further characteristics which differentiate a lettuce plant designated NUN 7824 LT from lettuce variety Sadawi and which can additionally be used to differentiate variety NUN 7824 LT and, e.g., one of its progeny, EDV or hybrid from Sadawi are listed in the following without being limiting:

Seeds of NUN 7824 LT are white to silver-grey color. In contrast, the seeds of Sadawi and Grand Rapids are black to grey-brown.

The shape of cotyledons of plants designated NUN 7824 LT are broad (see USDA descriptors). In contrast, the shapes of cotyledons of Sadawi-plants and Grand Rapids-plants are intermediate.

The concentration of anthocyanin in fourth leaves and mature leaves. The development of a red color in many plant species is dependent on the production of anthocyanin. The concentration of anthocyanin in fourth leaves and mature leaves of plants designated NUN 7824 LT is intense-to-moderate (see USDA descriptors). In contrast, the concentration of anthocyanin in fourth leaves of Sadawi-plants is moderate and Grand Rapids-plants lack anthocyanin (the leaves of this variety are yellow-green).

The glossy nature of their mature leaves. In contrast, the glossiness of mature leaves of Sadawi-plants and Grand Rapids-plants is moderate. According to USDA descriptors, glossiness of Salmon is comparable to glossiness of variety "Great Lakes", whereas glossiness of Sadawi and Grand Rapids is comparable to glossiness of variety "Salinas".

The average head weight of NUN 7824 LT-plants is, at mature harvest stage, at least about 5%, 10%, 12%, 13% or 14% higher than the head weight of Sadawi-plants, when grown under the same conditions. Harvest stage of Sadawi and Salmon, respectively, is, e.g., between 70 and 90 days after first water date, when grown under the same greenhouse conditions, e.g., 23° C. in daytime and 21° C. at night. Day length is kept at 18 hours by assimilation lights. The measurements where carried out with plants which were harvested 80 days after first water date.

Further differences can be seen in, e.g., Table 1.

The morphological and/or physiological differences between NUN 7824 LT and other known varieties, such as Sadawi or Grand Rapids (which is a standard regional check variety) can easily be established by growing NUN 7824 LT next to the other varieties (in the same field, greenhouse under the same environmental conditions), preferably in several locations which are suitable for lettuce cultivation, and measuring morphological and/or physiological characteristics of a number of plants (e.g., to calculate an average value (of at least 10 or even more plants which were grown under the same conditions) and to determine the variation range/uniformity within the variety). Comparative varieties which can be grown in the same field are Grand Rapids, Sadawi, Sucrine, Rosgem and others. These are commercially available.

For example, trials can be carried out in the Netherlands or the USA whereby e.g., seed characteristics, cotyledon characteristics, $4^{th}$ leaf characteristics, mature plant characteristics, such as plant head diameter, head shape, head size, head weight, butt and core characteristics, time of bolting (number of days from first water date to seed stalk emergence), seed stalk characteristics, bolter habit, maturity (earliness of harvest-mature head formation), regional and/or seasonal adaptation, pest and/or disease resistance/susceptibility can be measured and directly compared. Also resistance against physiological stresses, such as tipburn, heat-, drought-, cold-resistance, etc. and/or post-harvest characteristics of leaves can be compared, such as pink rib, russet spotting, rusty brown discoloration, internal rib necrosis (blackheart, grey rib, grey steak) and brown stain can be measured using known methods, e.g. as indicated in the USDA descriptors. The morphological and/or physiological characteristics may vary with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (see world wide net: http://www.rhs.org.uk/Plants/RHS-Publications/RHS-colour-charts).

Moreover, the present invention provides seeds of lettuce variety NUN 7824 LT, a representative sample of said seeds (at least 2500 seeds) having been deposited under the Budapest Treaty with Accession Number NCIMB 42217.

Seeds of NUN 7824 LT are obtainable by, e.g., growing plants from the seeds deposited under Accession number NCIMB 42217 and allowing, e.g., self-pollination or cross-pollination and collecting seeds from the resulting plants. The resultant NUN 7824 LT seeds can be grown to produce plants designated NUN 7824 LT. Moreover, a seed dedicated NUN 7824 LT also refers to a seed which plant grown thereof shows the essential characteristics of NUN 7824 LT, i.e. resistance against at least strains Bl:1 to Bl:27 of downy mildew (*Bremia lactucae*) as well as lettuce aphid *Nasonovia ribisnigri* NR:0 and the plant grown from a seed dedicated NUN 7824 LT has very intense red colored leaves.

In one embodiment, a plurality of NUN 7824 LT seeds are packaged into small and/or large containers (e.g., bags, cartons, cans, etc.). The seeds may be pelleted prior to packing (to form pills or pellets) and/or treated with various compounds, such as seed coatings.

Seed pelleting can be combined with film coating (Halmer, P. 2000. Commercial seed treatment technology. In: Seed technology and its biological basis. Eds: Black, M. and Bewley, J. D., pages 257-286). Pelleting creates round or rounded shapes, which are easily sown with modern sowing machines. A pelleting mixture typically contains seeds and at least glue and filler material. The latter could be, for example, clay, mica, chalk or cellulose. In addition, certain additives can be included to improve particular properties of the pellet, e.g., a seed treatment formulation comprising at least one insecticidal, acaricidal, nematicidal or fungicidal compound can be added directly into the pelleting mixture. A seed treatment formulation can include one of these types of compounds only, a mixture of two or more of the same type of compounds or a mixture of one or more of the same type of compounds with at least one other insecticide, acaricide, nematicide or fungicide.

Formulations especially suitable for the application as a seed treatment can be added to the seed in the form of a film coating including also the possibility of using the coating in or on a pellet, as well as including the seed treatment formulation directly into the pellet mixture. Characteristically, a film coating is a uniform, dust-free, water permeable film, evenly covering the surface of all individual seeds (Halmer, P. 2000. Commercial seed treatment technology. In: Seed technology and its biological basis. Eds: Black, M. and Bewley, J. D., pages 257-286). Besides the formulation, the coating mixture generally also contains other ingredients such as water, glue (typically a polymer), filler materials, pigments and certain additives to improve particular properties of the coating. Several coatings can be combined on a single seed.

In addition, several combinations with film coating are possible: the film coating can be added on the outside of the pellet, in between two layers of pelleting material, and directly on the seed before the pelleting material is added. Also more than 1 film coating layer can be incorporated in a single pellet. A special type of pelleting is encrusting. This technique uses less filler material, and the result is a 'minipellet'.

Seeds may also be primed. Of all the commercially planted vegetable seeds, lettuce is the most often primed.

Priming is a water-based process that is performed on seeds to increase uniformity of germination and emergence from the soil, and thus enhance vegetable stand establishment. Priming decreases the time span between the emergence of the first and the last seedlings. Methods how to prime lettuce seeds are well known in the art (see, e.g., Hill et al HortScience 42(6) 1436-1439, 2007 which is herewith incorporated by reference in its entirety).

Also provided are parts of the lettuce plants designated NUN 7824 LT such as microspores, pollen, ovaries, flowers, stalks, heads, ovules, leaves, shoots, seeds, embryos, embryo sacs cuttings, roots, cuttings, stems, cells, protoplasts, meristems, buds etc. of variety NUN 7824 LT, or parts of any of these. Such parts may be suitable for sexual reproduction, which include, without limitation microspores, pollen, flowers, ovaries, ovules, embryo sacs and egg cells, or which are suitable for vegetative reproduction, which include, without limitation cuttings, roots, stems, cells or protoplasts, leaves, meristems and buds.

Moreover, there is provided a cell or tissue culture from lettuce variety NUN 7824 LT in which the cell or tissue culture is derived from a tissue such as, for example and without limitation, leaves, pollen, embryos, cotyledon, hypocotyls, meristematic cells, roots, root tips, anthers, flowers, seeds or stems.

Also provided are lettuce plants grown from seeds, whereof representative seed having been deposited under Accession Number NCIMB 42217, regenerated from the above-described plant parts, or regenerated from the above-described tissue culture, having all of the morphological and physiological characteristics of lettuce variety NUN 7824 LT.

Lettuce plants can be produced by seeding directly in the ground (e.g., soil such as soil on a field) or by germinating the seeds in controlled environment conditions (e.g., greenhouses) and then transplanting the seedlings into the field. (See, e.g., Gonai et al., J. of Exp. Bot., 55(394), 111-118, 2004; Louise Jackson et al, Publication 7215 ISBN 978-1-60107-007-4 and Publication 7216 ISBN 978-1-60107-008-1 which are all herewith incorporated by reference and the world wide web at "anrcatalog.ucdavis.edu" search: lettuce for cultivation, harvesting, handling and postharvest methods commonly used).

Moreover, lettuce can be grown in hydroponic cultures as described in, e.g., US 2008/0222949 which is hereby incorporated by reference.

Hydroponics is the cultivation of plants without soil. There are 6 basic types of hydroponic systems: Wick, Raft (also called Water Culture), Ebb and Flow (also called Flood & Drain), Drip, Nutrient Film Technique, and Aeroponic. There are hundreds of variations on these basic types of systems, and most hydroponics systems can be described as a variation or combination of these six types.

In wick systems, plants are grown in a soil-less growing medium and a solution containing water and nutrients is delivered using wicks that absorb the solution from a reservoir and deliver the solution to the growing medium. The roots of the plants are optionally prevented from or allowed to grow in the solution.

In raft systems, plants are grown in a soil-less growth medium that is floated by a raft on the surface of a solution containing water and nutrients. The roots of the plants are optionally prevented from or allowed to grow in the solution.

In Ebb and Flow systems, plants are grown in a soil-less growth medium in a flooding tray. Solution containing water and nutrients is intermittently delivered to the flooding tray and then returned to a reservoir. The plant roots are directly or indirectly contacted by the solution in the flooding tray. Optionally the solution is delivered by a pump and returned by gravity.

In drip systems, plants are grown in a soil-less growing medium. A solution containing water and nutrients is delivered in drips to the growing medium. The solution that is not used by the plants is either recycled (recovery systems) or discarded (non-recovery systems). In recovery systems, although there often is a reservoir, the plant roots are typically prevented from growing directly in the solution.

Nutrient film technique (N.F.T.) systems constantly deliver a thin film of a nutrient and water containing solution. The plants are grown in a soil-less growth medium and the roots are allowed to grow outside the medium into the surrounding air or the plants are grown directly suspended in the air without a growing medium. The roots that grow in the air are constantly contacted by the thin film of solution. Typically the solution is recycled. Optionally the solution is delivered by a pump and returned by gravity.

Aeroponic systems deliver the solution as a fine spray. The plants are grown in a soil-less growth medium and the roots are allowed to grow outside the medium into the surrounding air or the plants are grown directly suspended in the air without a growing medium. The roots that grow in the air are intermittently sprayed or misted with a solution containing water and nutrients. The roots of the plants are optionally prevented from or allowed to grow in the solution.

Furthermore, different lettuce varieties may be grown as "composite lettuce" (see, e.g., EP 1 197 137 A1 which is hereby incorporated by reference).

In another embodiment, there is provided progeny of lettuce variety designated NUN 7824 LT produced by sexual or vegetative reproduction, e.g., grown from seeds, regenerated from the above-described plant parts, or regenerated from cell or tissue culture of the lettuce variety designated NUN 7824 LT, in which the reproduced (seeded or regenerated) plant has at least the essential morphological and physiological characteristics of lettuce variety designated NUN 7824 LT selected from the group consisting of resistance against downy mildew BL:1 to BL:27, resistance against lettuce aphid Nr:0 and very intensive red colored mature leaves. In one embodiment, said progeny of the lettuce variety designated NUN 7824 LT can be modified in one or more other characteristics, in which the modification is a result of, for example and without limitation, mutagenesis or transformation with a transgene. A progeny can be a first generation progeny or a progeny up to generation two, three, four, five, six, seven or even higher.

Thus, the invention also provides a method of producing plants of variety designated NUN 7824 LT, or a part thereof, comprising vegetative propagation of a plant designated NUN 7824 LT. In one embodiment, said vegetative propagation comprises regenerating a whole plant from a part of variety designated NUN 7824 LT. In one embodiment, said part of a plant is a cutting, root, sterm, cell, protoplast, leaf meristem or bud, a cell culture or a tissue culture. Thus, a vegetative propagated plant (or a part thereof) is provided having at least the essential morphological and physiological characteristics of a lettuce plant designated NUN 7824 LT when grown under the same environmental conditions. In some embodiments, said propagated plant has at least one more morphological and physiological characteristic in common with a lettuce plant designated NUN 7824 LT. Such characteristics are, e.g. the seed color, glossiness, shape of cotyledons etc. as outlined in this application.

Also provided is a method of producing a lettuce plant having a desired trait, wherein the method comprises transforming the lettuce plant of the invention with a transgene that confers the desired trait, wherein the transformed plant retains all the essential phenotypic and morphological characteristics of a NUN 7824 LT plant of the invention—i.e., resistance against downy mildew (*Bremia lactucae*) BI:1 to BI:27 and lettuce aphid (*Nasonovia ribisnigri*) Nr:0 and intensive red colored leaves—and contains the desired trait. Thus, a lettuce plant is provided which is produced by the method described above, wherein the plant comprises the desired trait and all of the physiological and morphological characteristics of a NUN 7824 LT plant.

The present invention also provides a plant grown from the seeds, regenerated from the above-described plant parts, or regenerated from the above-described tissue culture, having at least the essential morphological and physiological characteristics resistance against downy mildew (*Bremia lactucae*) BI:1 to BI:27 and lettuce aphid (*Nasonovia ribisnigri*) Nr:0 and intensive red colored leaves of lettuce variety NUN 7824 LT.

Furthermore, the invention provides for progeny of variety NUN 7824 LT such as progeny obtained by, e.g., selfing NUN 7824 LT one or more times and/or cross-pollinating NUN 7824 LT with another lettuce variety or with a lettuce plant of the invention one or more times. In particular, the invention provides for progeny that retain the essential morphological and physiological characteristics resistance against downy mildew (*Bremia lactucae*) BI:1 to BI:27 and lettuce aphid (*Nasonovia ribisnigri*) Nr:0 and intensive red colored leaves of NUN 7824 LT when grown under the same environmental conditions.

In still another embodiment, there is provided progeny of lettuce variety NUN 7824 LT produced by sexual or vegetative reproduction, grown from seeds, regenerated from the above-described plant parts, or regenerated from the above-described tissue culture of the lettuce variety or a progeny plant thereof, in which the regenerated plant has all of the morphological and physiological characteristics of lettuce variety NUN 7824 LT.

Moreover, also an Essentially Derived Variety (EDV) of a lettuce plant designated NUN 7824 LT is provided having one, two, three or more than three physiological and/or morphological characteristics which are different from those of NUN 7824 LT but which otherwise has the essential physiological and morphological characteristics of a lettuce plant designated NUN 7824 LT selected from the group consisting of resistance against downy mildew (*Bremia lactucae*) BI:1 to BI:27, resistance against lettuce aphid (*Nasonovia ribisnigri*) Nr:0 and very intensive red colored mature leaves.

In still another aspect, the present invention provides a method of producing a plant derived from NUN 7824 LT, the method comprising the steps of: (a) preparing a progeny plant derived from NUN 7824 LT, wherein said preparing comprises crossing a plant of NUN 7824 LT either as a male or as a female parent with a second plant or selfing NUN 7824 LT or vegetative reproduction of NUN 7824 LT.

In one embodiment, crossing a plant of NUN 7824 LT either as a male or as a female parent with a second plant refers to cross-pollination of two plants of NUN 7824 LT. In another embodiment, crossing a plant of NUN 7824 LT either as a male or as a female parent with a second plant refers to cross-pollination of NUN 7824 LT with a plant of another lettuce variety or wild In still yet another aspect; the present invention provides a method of producing a new plant comprising (a) crossing NUN 7824 LT or a progeny plant thereof with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from NUN 7824 LT. The plant derived from NUN 7824 LT may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from NUN 7824 LT is obtained which possesses some of the desirable traits of the line as well as potentially other selected traits.

In yet a further embodiment, the invention provides for a method of producing a new lettuce plant. The method comprises, crossing NUN 7824 LT, either as male or as female parent, with a second lettuce plant which can be a second lettuce plant of the same variety, a lettuce plant of a different variety or a wild relative of lettuce (e.g., L. virosa or L. serriola) or genetic transformation techniques to produce a progeny of NUN 7824 LT.

Thus, in one embodiment a method for developing a lettuce plant in a lettuce breeding program is provided, using a lettuce plant of the invention, or its parts as a source of plant breeding material. Suitable plant breeding techniques are recurrent selection, backcrossing, pedigree breeding, line selection, mass selection, mutation breeding and/or genetic marker enhanced selection. For example, in one aspect, the method comprises crossing a lettuce plant designated NUN 7824 LT or progeny thereof with a different lettuce plant selected from the group consisting of a plant of the same variety, a lettuce plant of a different variety or a wild relative of lettuce (e.g., L. virosa or L. serriola), and wherein one or more offspring of the crossing are subject to one or more plant breeding techniques selected from the group consisting of recurrent selection, backcrossing, pedigree breeding, line selection, mass selection, mutation breeding and genetic marker enhanced selection (see e.g. Principles of Plant Genetics and Breeding, 2007, George Acquaah, Blackwell Publishing, ISBN-13: 978-1-4051-3646-4 which is herewith incorporated by reference).

In one embodiment, Pedrigee selection is used as breeding method for developing a lettuce variety. Pedigree selection, also known as the "Vilmorin system of selection," is described in Fehr, W., *Principles of Cultivar Development*, Volume I, MacMillan Publishing Co., which is hereby incorporated by reference.

In general, selection is first practiced among $F_2$ plants. In the next season, the most desirable $F_3$ lines are first identified, then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents may be crossed using an emasculated female and a pollen donor (male) to produce $F_1$ offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes. Additionally, any breeding method involving selection of plants for the desired phenotype can be used in the method of the present invention.

The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

Thus, progeny in connection with Pedrigee selection are either the generation (seeds) produced from the first cross (F1) or selfing (S1), or any further generation produced by crossing and/or selfing (F2, F3, F4, F5, F6, F7, etc.) and/or backcrossing (BC1, BC2, BC3, BC4, BC5, BC6, BC7, etc.) one or more selected plants of the F1 and/or S1 and/or BC1 generation (or plants of any further generation, e.g. the F2) with another lettuce plant (and/or with a wild relative of lettuce). Using common breeding methods such as backcrossing or recurrent selection, one or more specific characteristics may be introduced into NUN 7824 LT, to provide an EDV of NUN 7824 LT.

General crossing methods for lettuce are, e.g., described in US 2009/0271897 A1 which is herewith incorporated by reference. Such methods include but are not limited to:

Manual removal of anther tubes from flowers, misting the designated male flowers to wash the pollen off prior to fertilization and pollen from another variety or donor parent is then introduced by gently rubbing the stigma and style of the donor parent to the maternal parent. Tags with the pertinent information on date and pedigree are then secured to the flowers in order to keep track. About 3 weeks after pollination, seeds are harvested when the involucre have matured. The seeds are eventually sown and in the presence of markers such as leaf color or leaf margins, the selfed or maternal seedlings or plants are identified. Generally, in case of crossing with a plant of a different variety, there are no visible markers and breeders must wait until the F2 generations when expected segregation patterns for the genetic character of interest can be followed.

Use of male sterility systems. Non-limiting examples are engineering of male sterility in lettuce by expression of a ribonuclease gene under the control of a tapetum-specific promoter (see Reynaerts et al., Scientia Horticulturae (1993) 55 (1-2): 125-129 which is herewith incorporated). Other male sterile systems include the expression of beta-glucanase via a tapetum-specific promoter (see Curtis et al., Plant Science Limerick (1996) 113(1): 113-119). Genetically engineered sterility is also available.

Many useful traits that can be introduced by backcrossing, as well as directly into a plant, are those which are introduced by genetic transformation techniques. Genetic transformation may therefore be used to insert a selected transgene into the lettuce line of the invention or may, alternatively, be used for the preparation of trans genes which can be introduced by backcrossing. Methods for the transformation of plants, including lettuce, are well known to those of skill in the art.

Vectors used for the transformation of lettuce cells are not limited so long as the vector can express an inserted DNA in the cells. For example, vectors comprising promoters for constitutive gene expression in lettuce cells (e.g., cauliflower mosaic virus 35S promoter) and promoters inducible by exogenous stimuli can be used. Examples of suitable vectors include pBI binary vector. The "lettuce cell" into which the vector is to be introduced includes various forms of lettuce cells, such as cultured cell suspensions, protoplasts, leaf sections, and callus.

A vector can be introduced into lettuce cells by known methods, such as the polyethylene glycol method, polycation method, electroporation, *Agrobacterium*-mediated transfer, particle bombardment and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner. An example of electroporation of lettuce protoplasts is presented in Chupeau et al. (1989; Bio/Technology 7; 503-8).

When using microprojectile bombardment, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target lettuce cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. Examples involving microprojectile bombardment transformation with lettuce can be found in, for example, Elliott et al. (2004; Phys. Rev. Lett. 92, 095501) and Molinier et al. (2002).

Agrobacterium-mediated transfer is another widely applicable system for introducing gene loci into plant cells. Modern Agrobacterium transformation vectors are capable of replication in E. coli as well as Agrobacterium, allowing for convenient manipulations (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, Agrobacterium containing both armed and disarmed Ti genes can be used for transformation.

The use of Agrobacterium-mediated plant integrating vectors to introduce DNA into plant cells is well known in the art (Fraley et al., 1985; U.S. Pat. No. 5,563,055). For example, U.S. Pat. No. 5,349,124 describes a method of transforming lettuce plant cells using Agrobacterium-mediated transformation. By inserting a chimeric gene having a DNA coding sequence encoding for the full-length B.t. toxin protein that expresses a protein toxic toward Lepidopteran larvae, this methodology resulted in lettuce having resistance against such insects.

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994) and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for lettuce plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunl, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the lettuce lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Non-limiting examples of particular genes and corresponding phenotypes one may choose to introduce into a lettuce plant include one or more genes for insect tolerance, such as a Bacillus thuringiensis (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a Bacillus insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to Agrobacterium strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Also provided is a method of producing a hybrid lettuce seed comprised of crossing a first parent lettuce plant with a second parent lettuce plant and harvesting the resultant hybrid lettuce seed, in which the first parent lettuce plant or the second parent lettuce plant is the lettuce variety NUN 7824 LT. Accordingly, a hybrid lettuce plant produced from crossing a first parent lettuce plant with a second parent lettuce plant and harvesting the resultant hybrid lettuce seed, wherein said first parent lettuce plant or said second parent lettuce plant is a lettuce plant designated NUN 7824 LT is provided, as well.

The invention provides for methods of producing EDVs (Essentially Derived Varieties), which retain at least the essential morphological and physiological characteristics of NUN 7824 LT selected from the group consisting of downy mildew (*Bremia lactucae* Regal) BL:1 to BL:27, resistance against lettuce aphid (*Nasonovia ribisnigri*) Nr:0 and very intensive red colored mature leaves, which may differ from a lettuce plant designated NUN 7824 LT in one, two, three or more further morphological and/or physiological characteristics, but which are still genetically closely related to NUN 7824 LT. The relatedness can, for example be determined by fingerprinting techniques (e.g., making use of isozyme markers and/or molecular markers such as SNP markers, AFLP markers, microsatellites, minisatellites, RAPD markers, RFLP markers and others). An plant is "closely related" to NUN 7824 LT if its DNA fingerprint is at least 80%, 90%, 95%, 97% or 98% identical to the fingerprint of NUN 7824 LT. In a preferred embodiment amplified fragment length polymorphism (AFLP) markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (van Eeuwijk and Law (2004), Euphytica 137: 129-137).

By crossing and/or selfing also (one or more) single traits may be introduced into NUN 7824 LT (e.g., using backcrossing breeding schemes), while retaining the remaining morphological and physiological characteristics of NUN 7824 LT. For example, disease resistance genes may be introduced, genes responsible for one or more quality traits (such as head quality), yield, etc. Both single genes (dominant or recessive) and one or more QTLs (quantitative trait loci) may be transferred into NUN 7824 LT by breeding with NUN 7824 LT.

Any pest or disease resistance genes may be introduced into NUN 7824 LT, progeny thereof or into an EDV of NUN 7824 LT. Resistance against one or more of the following diseases is preferably introduced into plants of the invention: downy mildew, *sclerotinia* rot, botrytis, powdery mildew, anthracnose, bottom rot, corky root rot, lettuce mosaic virus, big vein, lettuce aphid, beet western yellows and aster yellows. Resistance against one or more of the following pests is preferably present or introduced into plants of the invention: *Sclerotinia minor* (leaf drop), *Sclerotinia sclerotiorum* (leaf drop), *Rhizoctonia solani* (bottom drop), *Erysiphe cichoracearum* (powdery mildew), *Fusarium oxysporum* f. sp. *Lactucae* (fusarium wilt) resistance. Other resistance genes, against pathogenic viruses (e.g. Lettuce infectious yellows virus (LIYV), lettuce mosaic virus (LMV), Cucumber mosaic virus (CMV), Beet western yellows virus (BWYV), Alfalfa mosaic virus (AMV)), fungi, bacteria or lettuce pests may also be introduced. In one embodiment resistance against *Nasonovia ribisnigri* biotype Nr:1 is introduced into NUN 7824 LT. Resistance has been identified in various CGN accessions (anonymous internet publication of 4 Nov. 2008 entitled "Resistance against the lettuce aphid *Nasonovia ribisnigri*", priorartdatabase.com/IPCOM/000176078).

In one embodiment, NUN 7824 LT may also be mutated (by e.g. irradiation, chemical mutagenesis, heat treatment, etc.) and mutated seeds or plants may be selected in order to change one or more characteristics of NUN 7824 LT. Also natural mutants may be identified and used in breeding. Methods such as TILLING and/or EcoTILLING may be applied to lettuce populations in order to identify mutants. Similarly, NUN 7824 LT may be transformed and regenerated, whereby one or more chimeric genes are introduced into the variety. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 7824 LT, or progeny thereof, by transforming NUN 7824 LT or progeny thereof with a transgene that confers the desired trait, wherein the transformed plant retains all the morphological and physiological characteristics of NUN 7824 LT or the progeny thereof and contains the desired trait.

The invention also provides for progeny of lettuce variety NUN 7824 LT obtained by further breeding with NUN 7824 LT. In one aspect progeny are F1 progeny obtained by crossing NUN 7824 LT with another plant or S1 progeny obtained by selfing NUN 7824 LT. Also encompassed are F2 progeny obtained by selfing the F1 plants. "Further breeding" encompasses traditional breeding (e.g., selfing, crossing, backcrossing), marker assisted breeding, and/or mutation breeding. In one embodiment, the progeny have all the physiological and morphological characteristics of variety NUN 7824 LT when grown under the same environmental conditions. In another embodiment the progeny are EDVs and/or have one, two, or three distinct traits (qualitative or quantitative) introduced into NUN 7824 LT, while retaining all the other physiological and morphological characteristics of variety NUN 7824 LT when grown under the same environmental conditions.

The variety NUN 7824 LT, or its progeny (e.g. an EDV), can also be reproduced using vegetative reproduction methods. Therefore, the invention provides for a method of producing plants, or a part thereof, of variety NUN 7824 LT comprising vegetative propagation of variety NUN 7824 LT. Vegetative propagation comprises regenerating a whole plant from a part of variety NUN 7824 LT, such as a cutting, a cell culture or a tissue culture (e.g., in vitro meristem culture, see Murakami and Oka, 1996, Plant Tissue Culture Letters 13(3), 339-341).

The invention also provides for a vegetatively propagated plant of variety NUN 7824 LT, or a part thereof, having all the morphological and physiological characteristics of NUN 7824 LT when grown under the same environmental conditions.

In one aspect haploid plants and/or double haploid plants of NUN 7824 LT are encompassed herein. Haploid and double haploid (DH) plants can for example be produced by anther or microspore culture and regeneration into a whole plant. For DH production chromosome doubling may be induced using known methods, such as colchicine treatment or the like.

Also provided are plant parts derived from variety NUN 7824 LT, or from a vegetatively propagated plant of NUN 7824 LT, being selected from the group consisting of: harvested (mature or immature) leaves or parts thereof, pollen, ovules, cells, heads, cotyledons, seeds or parts thereof, stalks or parts thereof, roots or parts thereof, cuttings, or parts thereof, flowers, florets, or flower buds.

In one embodiment, the invention provides for extracts of a plant described herein and compositions comprising or consisting of such extracts. In a preferred embodiment, the extract consists of or comprises tissue of a plant described herein or is obtained from such tissue. For example sesquiterpene-lacotnes such as lactucin, lactucid or lactucopicrin; or triterpenes such as amyrin, lactucerol or taraxasterol cyanine may be an extract obtained from leaf tissue and used to make a health-beneficial composition (e.g., a pharmaceutical composition).

The invention also provides for a food or feed product comprising or consisting of a plant part described herein and/or an extract from a plant part described herein. The food or feed product may be fresh or processed, e.g., canned, steamed, boiled, fried, blanched and/or frozen etc.

A lettuce plant designated NUN 7824 LT, a progeny thereof, a derived variety thereof (such as EDV), and parts of the afore-mentioned plants/varieties can be suitably packed for, e.g., transport, and/or sold fresh. Such parts encompass any cells, tissues and organs obtainable from the seedlings or plants, such as but not limited to: heads, cuttings, pollen leaves, parts of leaves, and the like. Leaves may be harvested immature, as baby-leaf, or mature. A plant, plants or parts thereof may be packed in a container (e.g., bags, cartons, cans, etc.). alone or together with other plants or materials. Parts can be stored and/or processed further. Encompassed are therefore also food or feed products comprising one or more of such parts, such leaves or parts thereof obtainable from NUN 7824 LT plant, a progeny thereof a derived variety thereof (such as EDV), and parts of the afore-mentioned plants/varieties.

For example, containers such as cans, boxes, crates, bags, cartons, Modified Atmosphere Packagings, films (e.g. biodegradable films), etc. comprising plant parts of plants (fresh and/or processed) designated NUN 7826 LT are also provided herein.

The "very intensive red color" of a plant in accordance with the present invention can be determined by comparing the color of, e.g., fourth or mature leaves with baby, fourth or mature leaves of a Sadawi plant grown under the same conditions. The skilled person can, e.g., use a RHS colour chart: 2007 (The Royal Horticultural Society, charity No: 222879, PO Box 313 London SW1P2PE; sold by, e.g., TORSO-VERLAG, Obere Grüben 8•D-97877 Wertheim, Article-No.: Art62-00008 EAN-Nr.: 4250193402112). The RHS Colour Chart is the standard reference for plant color identification. For example, without limiting the scope of the present invention, fourth leaves and mature leaves of NUN 7824 LT exhibit a color which is normally even darker than N186 (first square) of the RHS colour chart, whereas fourth and mature leaves of Sadawi exhibit a color which is slightly brighter than N187 (first square) of the RHA colour chart. N187 (first Square) again is brighter than N186 (first square). The first square of the RHS colour chart is the outer square of the slights (which are connected with each other at the end of the inner color square).

However, the skilled person will understand that the color of a plant also depends on its growing condition like water, light, soil etc. Thus, the skilled person understands that the colour chart may exhibit different correlation results when plants are examined which grew under different conditions. However, in one embodiment, the color of fourth leaves and mature leaves of NUN 7824 LT plants will always be at least one category darker than those of Sadawi forth and mature leaves which were taken from plants grown under the same conditions as the corresponding NUN 7824 LT plants.

Moreover, the concentration of anthocyanins can be determined by using standard methods known in the art. One of these methods is, e.g., described in US 2009/0106867 which is herewith incorporated by references in its entirety. For example, a headed and mature lettuce plant is harvested and outer leaves are taken off. In general the four oldest leaves can be regarded as outer leaves. The skilled person is aware that the oldest leaves of a lettuce plant are located at the outer part of the centre of the lettuce plant.

The "centre" of a plant is the part of a lettuce plant where the leaves are attached to the root system of the plant. In other words, the centre of a plant is the area where new leaves are formed. The remaining lettuce leaves are used for the analysis. At least ten leaves with a length of 3 cm or longer should be used.

The leaves can be pulverized and analysed for anthocyanins. Pulverization can be achieved by, e.g., freezing the leaves and grinding them with a sledgehammer and further grinding the crude powder with a knife mill such as a Grindomix GM 200 (Retsch, 5" 3000 rpm followed by 5" 5000 rpm) using the free floating lid in presence of liquid nitrogen to achieve a powder for analysis of anthocyanins.

As an example for the analysis, said powder is added to a solution of HCl in methanol (e.g. 1 M HCl in 50% methanol). The amount of sample depends from the color. Generally 2-40 ml/g sample is used. The used volume (ml) is noted. A part of the solution is freed from insoluble parts, e.g., by using a centrifuge at 4° C., 13000 rpm for around 4 min.

The spectrum of 360-900 nm is measured and the absorbance at 523 nm (if necessary after dilution with extraction liquid) and the maximum wavelength ($\lambda_{max}$) are determined. $\lambda_{max}$ should be close to 523 nm.

Moreover, chlorophylls are measured by immediately adding 100% methanol to the test sample of the anthocyanin analysis. The volume (ml) used is noted.

The spectrum of 360-900 nm is measured and the absorbance at 665 nm (if necessary after dilution with extraction liquid) and the maximum wavelength ($\lambda_{max}$) determined. $\lambda_{max}$ should be close to 665 nm.

The A523 and A665 are corrected to represent the absorbance of a solution of 1 g fresh weight in 10 ml extraction volume. The corrected A523 and A665 are calculated with a correction for weighted sample (in g), extraction volume (in ml) and if necessary dilution using the following formula:

$$A_{corrected} = \frac{A_{measured} * extr. \text{ volume}}{weight * 10} * dilution$$

The ratio A523/A665 is calculated.

In one embodiment, NUN 7824 LT plants can be distinguished from Sadawi plants which were grown under the same conditions by measuring the chlorophyll and anthocyanin absorbance and calculating the anthocyanin/chlorophyll-ratio observed on lettuce. At least 5, 7, 10, 15 plants should be used to calculate the mean ratio. The skilled person understands that the amount of anthocyanin and chlorophyll depends to some extend from the growing conditions of a plant. Thus, the skilled person will know typical growing conditions for lettuce of the types described herein. In one embodiment, the mean anthocyanin/chlorophyll-ratio of NUN 7824 LT is at least 1, 2, 3, 4, 5, 6 units higher compared to the anthocyanin/chlorophyll-ratio of Sadawi when grown under the same conditions (e.g., when the mean anthocyanin/ chlorophyll-ratio of Sadawi is 15 than the mean anthocyanin/chlorophyll-ratio of NUN 7824 LT is at least 16, 17, 18, 19, 20, 21).

All documents (e.g., patent publications) are herein incorporated by reference in their entirety.

Representative seeds of NUN 7824 LT were deposited on Jan. 30, 2014 with the NCIMB, Ferguson Building, Craibstone Estate, Bucksburn, Aberdeen AB21 9YA, United Kingdom under the deposit accession numbers NCIMB 42217.

Various modifications and variations of the described products and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

EXAMPLES

Development of NUN 7824 LT

The variety NUN 7824 LT was developed from an initial cross between two different lettuce varieties. The female and male parents were crossed to produce hybrid (F1) seeds. After the cross, F1 plants were self pollinated. From the second to the fifth generation pedigree selection was performed. From the sixth till the seventh generation line selection was performed.

Variety NUN 7824 LT has been observed for at least two generations in different trials on different locations and during seed increase and is uniform.

Moreover, variety NUN 7824 LT has been observed in different trials on different locations for two generations and during seed increase and is stable.

The variety is, therefore, uniform and genetically stable. This has been established through evaluation of horticultural characteristics. Independent seed production events resulted in no observable deviation in genetic stability.

Seeds were obtained from plants finally selected in the process of breeding the new variety "Salmon". A total of 2500 seeds of the variety NUN 7824 LT (also called "Salmon") were deposited by Nunhems B. V. on Jan. 30, 2014, at the NCIMB Ltd., Ferguson Building, Craibstone Estate, Bucksburn, Aberdeen AB21 9YA, United Kingdom (NCIMB). The deposit has been assigned Accession Number NCIMB 42217.

Applicants hereby waive any restrictions on the public availability of the deposited material from the NCIMB or ATCC, once a US patent has been granted on this application. However, Applicants have no authority to waive any restrictions imposed by law on the transfer, importation or (commercial) use of biological material. The Applicant does not waive any infringement of its rights granted under a patent on this application, or under the Plant Variety Protection Act (7 USC 2321 et seq.).

The seeds of NUN 7824 LT can be grown to produce plants and parts thereof (e.g. heads or leaves). The variety NUN 7824 LT can be propagated by seeds or vegetative.

Salmon characteristics were compared with those of Sadawi and Grand Rapids according to standards of the U.S. Department of Agriculture, Agricultural Marketing Service, Science and Technology, Plant Variety Protection Office, Beltsville, Md. 20705. The trials were carried out on behalf of Nunhems B. V. (the Netherlands) by Naktuinbouw, Roelofarendsveen (the Netherlands) (Planting date: Aug. 18, 2010, duration 80 and 85 days, respectively).

The variety Salmon has very good plant development and stress tolerance, a very intense red leaf color and glossy leaves.

Characteristics of NUN 7824 LT

Table 1 shows the USDA descriptors of NUN 7824 LT (Salmon; this application), Sadawi (Enza Zaden) and Grand Rapids. 20 plants or plant parts were randomly selected from two replications of 100 plants each. These 20 plants were used to measure characteristics. Some of the most significant differences are highlighted in bold.

TABLE 1

| USDA number | USDA descriptor | NUN 7824 LT | Sadawi | Grand Rapids |
|---|---|---|---|---|
| 1 | Plant type<br>1 = cutting/leaf | 1 | 1 | 1 |
| 2 | Seed<br>1 = white, 2 = black, 3 = brown | 1 | 2 | 2 |
| 3 | Cotyledon to fourth leaf stage | | | |
| | Shape of Cotyledons<br>1 = broad, 2 = intermediate, 3 = spatulate | 1 | 2 | 2 |
| | Shape of fourth leaf<br>4 = elongated, 6 = pinnately lobed | 6 | 6 | 4 |
| | Length/width index of fourth leaf (L/W * 10) | 22 | 22 | 20 |
| | Apical margin<br>1 = entire, 5 = coarsely dentate, 7 = lobed | 7 | 7 | 1 |
| | Basal margin<br>1 = entire, 5 = coarsely dentate, 7 = lobed | 7 | 7 | 5 |
| | Undulation<br>1 = flat, 2 = slight, 3 = medium | 2 | 2 | 3 |
| | Green color<br>1 = yellow green, 7 = grey green<br>Anthocyanin: | red | red | 1 |
| | Distribution<br>1 = absent, 4 = throughout | 4 | 4 | 1 |
| | Concentration<br>1 = light, 2 = moderate, 3 = intense | 3 to 2 | 2 | — |
| | Rolling<br>1 = absent, 2 = present | 2 | 2 | 2 |
| | Cupping<br>1 = uncupped, 3 = markedly | 1 | 1 | 1 |
| | Reflexing<br>2 = apical margin, 3 = lateral margins | 2 and 3 | 2 and 3 | 2 and 3 |
| 4 | Mature leaves (harvest mature outer leaves):<br>Margin: | | | |
| | Incision depth<br>1 = absent/shallow (Dark Green Boston) | 1 lobed | 1 lobed | 1 shallow |
| | Indentation<br>1 = entire, 2 = shallowly dentate | 1 | 1 | 2 |
| | Undulations of the apical margin<br>1 = absent/slight, 2 = moderate | 1 | 1 | 2 |
| | Green color<br>1 = very light green,<br>2 = light green,<br>3 = medium green, 6 = other<br>Anthocyanin: | 6<br>very intense red | 6<br>Intense red | 2<br>Light yellow green |
| | Distribution<br>1 = absent, 4 = throughout (Prize Head) | 4 | 4 | 1 |
| | Concentration<br>1 = light, 2 = moderate,<br>3 = intense | 3<br>Very intense | 3<br>intense | — |

TABLE 1-continued

| USDA number | USDA descriptor | NUN 7824 LT | Sadawi | Grand Rapids |
|---|---|---|---|---|
| | Size | 2 | 2 | 2 |
| | 1 = small, 2 = medium, 3 = large | | | |
| | Glossiness | 3 | 2 | 2 |
| | 1 = dull, 2 = moderate, 3 = glossy | | | |
| | Blistering | 1 | 1 | 2 |
| | 1 = absent/slight, 2 = moderate, 3 = strong | | | |
| | Leaf thickness | 1 | 1 | 1 |
| | 1 = thin, 2 = intermediate, 3 = thick | | | |
| | Trichomes | 1 | 1 | 1 |
| | 1 = absent, 2 = present | | | |
| 5 | Plant | | | |
| | Spread of frame leaves | 35 cm | 32 cm | 37 cm |
| | Head diameter (market trimmed with single cap leaf) | 35 cm | 32 cm | 37 cm |
| | Head shape | 5 | 5 | 5 |
| | 1 = flattened, 5 = non-heading | | | |
| | Head size class | 2 to 1 | 2 to 1 | 2 |
| | 1 = small, 2 = medium, 3 = large | | | |
| | Head per carton | — | — | — |
| | Head weight | 263 g | 232 g | 361 g |
| | Head firmness | 1 | 1 | 1 |
| | 1 = loose, 4 = very firm | | | |
| 6 | Butt | | | |
| | Shape | 3 | 3 | 3 |
| | 1 = slightly concave, 2 = flat, 3 = rounded | | | |
| | Midrib | 3 | 3 | 3 |
| | 3 = prominently raised | | | |
| 7 | Core | | | |
| | Diameter at base of head | 24 mm | 20 mm | 28 mm |
| | Ratio of head diameter/core diameter | 14.5 | 15.8 | 13.2 |
| | Core height from base of head to apex | 47 mm | 44 mm | 41 mm |
| 8 | Bolting | | | |
| 9 | Maturity (earliness of harvest-mature head formation) | | | |
| | Season: summer | 80 days | 80 days | 85 days |
| | Number of days from first water date to harvest (note: First water date is the date seed first receives adequate moisture to germinate. This often equals planting date). | | | |
| 10 | Adaptation | | | |
| 11 | Viral Diseases | | | |
| | 1 = immune, 3 = resistant, 5 = moderately resistant, 7 = susceptible, 9 = highly susceptible | | | |
| | Big Vein virus | Not tested | Not tested | Not tested |
| | Lettuce mosaic virus | 7 | Not tested | Not tested |
| | Cucumber Mosaic | Not tested | Not tested | Not tested |
| | Tomato Bushy Stunt | Not tested | Not tested | Not tested |
| | Turnip Mosaic | Not tested | Not tested | Not tested |
| | Beet Western Yellows | Not tested | Not tested | Not tested |
| | Lettuce Infectious Yellows | Not tested | Not tested | Not tested |

The invention claimed is:

1. A lettuce plant designated NUN 7824 LT, referred to as Salmon, representative seed of which having been deposited under Accession Number NCIMB 42217.

2. A seed designated NUN 7824 LT, representative seed having been deposited under Accession Number NCIMB 42217.

3. A part of the plant of claim 1, wherein the part is a leaf or a part thereof.

4. A part of the plant of claim 1, wherein said part of the plant is suitable for vegetative reproduction.

5. A part of the plant of claim 1, wherein said part of the plant is suitable for sexual reproduction.

6. A cell or tissue culture of the lettuce plant of claim 1.

7. A lettuce plant that has resistance against downy mildew (*Bremia lactucae* Regal) BL:1 to BL:27, resistance against lettuce aphid (*Nasonovia ribisnigri*) Nr:0 and very intensive red colored mature leaves and which is grown from the seed of claim 2.

8. A lettuce plant that has resistance against downy mildew BL:1 to BL:27, resistance against lettuce aphid Nr:0 and very intensive red colored mature leaves, which is regenerated from the part of the plant of claim 4.

9. A lettuce plant that has resistance against downy mildew BL:1 to BL:27, resistance against lettuce aphid Nr:0 and very intensive red colored mature leaves, which is regenerated from the cell or tissue culture of claim 6.

10. A method of producing a lettuce plant, comprising crossing the plant of claim 1 with a second lettuce plant one or more times, and selecting progeny from said crossing.

11. A method of producing a lettuce plant, comprising selfing the plant of claim 1 one or more times, and selecting progeny from said selfing.

12. Progeny of lettuce variety designated NUN 7824 LT obtained by further breeding with said variety, wherein said progeny has at least the essential physiological and morphological characteristics of the variety designated NUN 7824 LT, wherein said essential physiological and morphological characteristics include resistance against downy mildew BL:1 to BL:27, resistance against lettuce aphid Nr0, less than 10% of the mid-ribs of all mature leaves being green, and a cutting plant type, wherein representative seed of said lettuce variety designated NUN 7824 LT has been deposited under Accession Number NCIMB 42217.

13. The progeny of claim 12, wherein said progeny further has at least one of the physiological and morphological characteristics selected from the group consisting of white to silver grey seed color, broad shape of cotyledons (according to USDA descriptors), higher concentration of anthocyanin in fourth leaves compared to lettuce variety Sadawi, glossy mature leaves (according to USDA descriptors), higher average head weight of at least 5% at mature harvest stage compared to the average head weight of lettuce variety Sadawi at the same mature harvest stage, when grown under the same conditions.

14. An Essentially Derived Variety having at least one, two or three physiological and/or morphological characteristics which are different from those of NUN 7824 LT and which otherwise has the essential physiological and morphological characteristics of a lettuce plant designated NUN 7824 LT, wherein said essential physiological and morphological characteristics include resistance against downy mildew BL:1 to BL:27, resistance against lettuce aphid Nr:0, less than 10% of the mid-ribs of all mature leaves being green. and a cutting plant type, wherein representative seed of NUN 7824 LT has been deposited under Accession Number NCIMB 42217.

15. A method of producing a hybrid lettuce seed, comprising crossing a first parent lettuce plant with a second parent lettuce plant and harvesting the resultant hybrid lettuce seed, wherein said first parent lettuce plant or said second parent lettuce plant is a lettuce plant designated NUN 7824 LT, wherein representative seed of said lettuce plant designated NUN 7824 LT has been deposited under Accession Number NCIMB 42217.

16. A hybrid lettuce plant produced from crossing a first parent lettuce plant with a second parent lettuce plant and harvesting the resultant hybrid lettuce seed, wherein said first parent lettuce plant or said second parent lettuce plant is a lettuce plant designated NUN 7824 LT, wherein representative seed of said lettuce plant designated NUN 7824 LT has been deposited under Accession Number NCIMB 42217.

17. Package comprising leaves or parts thereof of a plant of claim 3.

18. Package comprising the seed of claim 2.

19. Seed pellet comprising the seed of claim 2.

20. A food or feed product comprising a plant part of claim 1.

21. A method of introducing a single locus conversion into a lettuce plant designated NUN 7824 LT comprising
(a) crossing a plant of variety designated NUN 7824 LT with a second plant comprising a desired single locus to produce F1 progeny plants;
(b) selecting F1 progeny plants that have the single locus to produce selected F1 progeny plants;
(c) crossing the selected progeny plants with at least a first plant designated NUN 7824 LT to produce backcross progeny plants;
(d) selecting backcross progeny plants that have the single locus and essential physiological and morphological characteristics of a plant designated NUN 7824 LT to produce selected backcross progeny plants; and
(e) repeating steps (c) and (d) one or more times in succession to produce selected second or higher backcross progeny plants that comprise the single locus and otherwise comprise at least the essential physiological and morphological characteristics of a plant designated NUN 7824 LT, wherein representative seed of said plant designated NUN 7824 LT has been deposited under Accession Number NCIMB 42217.

22. The method of claim 21, wherein the single locus confers a trait, wherein the trait is pest resistance or disease resistance.

23. The method of claim 22, wherein the single locus confers a trait, wherein the trait is resistance against *Nasonovia ribisnigri* Nr:1.

* * * * *